US008575546B2

(12) United States Patent
Nagamine

(10) Patent No.: US 8,575,546 B2
(45) Date of Patent: Nov. 5, 2013

(54) NONDESTRUCTIVE INSPECTION APPARATUS AND NONDESTRUCTIVE INSPECTION METHOD FOR COMPOSITE STRUCTURE

(75) Inventor: Kanetada Nagamine, Kashiwa (JP)

(73) Assignee: Inter-University Research Institute Corporation High Energy Accelerator Research Organization, Tsukuba-Shi (JP)

( * ) Notice: Subject to any disclaimer, the term of this patent is extended or adjusted under 35 U.S.C. 154(b) by 2 days.

(21) Appl. No.: 12/735,887

(22) PCT Filed: Feb. 23, 2009

(86) PCT No.: PCT/JP2009/053140
§ 371 (c)(1),
(2), (4) Date: Aug. 24, 2010

(87) PCT Pub. No.: WO2009/107575
PCT Pub. Date: Sep. 3, 2009

(65) Prior Publication Data
US 2011/0001046 A1 Jan. 6, 2011

(30) Foreign Application Priority Data

Feb. 25, 2008 (JP) ................................. 2008-043595

(51) Int. Cl.
*G01N 23/20* (2006.01)
(52) U.S. Cl.
USPC ............................ 250/306; 250/307; 250/308
(58) Field of Classification Search
USPC ....................................................... 250/306
See application file for complete search history.

(56) References Cited

U.S. PATENT DOCUMENTS

| 5,821,541 | A | * | 10/1998 | Tumer | 250/370.09 |
| 7,633,062 | B2 | * | 12/2009 | Morris et al. | 250/308 |
| 2005/0195552 | A1 | * | 9/2005 | Torii | 361/212 |
| 2006/0180753 | A1 | * | 8/2006 | Bryman | 250/266 |

FOREIGN PATENT DOCUMENTS

JP 2008-014816 1/2008

OTHER PUBLICATIONS

Schultz, L. J. "Cosmic Ray Muon Radiography", a dissertation for the degree of Doctor of Philosophy in Electrical and Computer Engineering, Portland State University 2003.*
Schultz, L. J. "Cosmic Ray Muon Radiography", a dissertation for the degree of Doctor of Philosophy in Electrical and Computer Engineering, Portland State University 2003, pp. 50-83.*
Kanetada Nagamine, "Muon Radiography", Genshikaku Kenkyu, Oct. 31, 2007; vol. 52, Supplement 2, pp. 43 to 52.

* cited by examiner

*Primary Examiner* — Phillip A Johnston
(74) *Attorney, Agent, or Firm* — Manabu Kanesaka

(57) ABSTRACT

The invention provides a nondestructive inspection apparatus and nondestructive inspection method for inspecting the inside of a surface layer of a composite structure using cosmic-ray muons. The nondestructive inspection apparatus is to inspect the inside of the surface layer of a composite structure 11 using cosmic-ray muons 12 incoming substantially in the horizontal direction with being spin polarized by a given amount in the incoming direction, and has positron/electron amount detecting means 13 for detecting a positron/electron amount reflection-emitted having a characteristic time constant in the direction opposite to the incoming direction of the cosmic-ray muons 12 by the decay of the cosmic-ray muons 12 stopping inside the composite structure 11, and radiography data processing means 14, 15, 16 for data-processing a state of the second substance 11-2 different from the first substance 11-1 of the surface layer existing inside the surface layer of the composite structure 11 as radiography to output, from the positron/electron amount detected in the positron/electron detecting means 13.

13 Claims, 11 Drawing Sheets

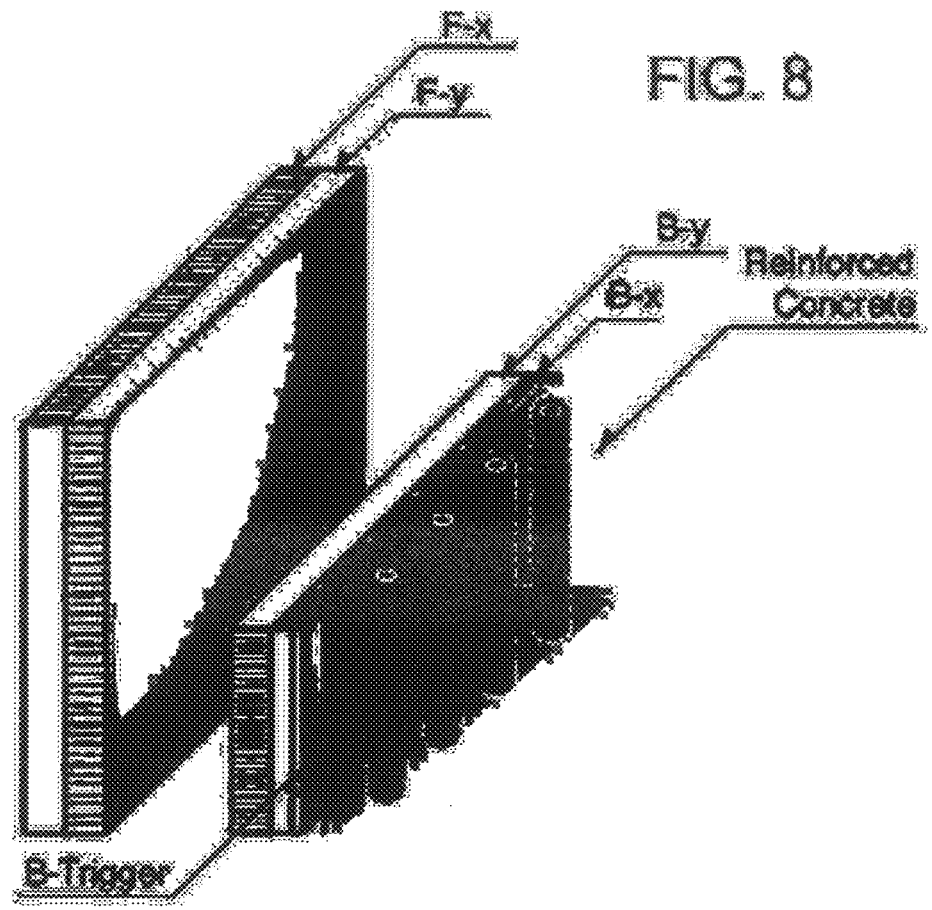
FIG. 8
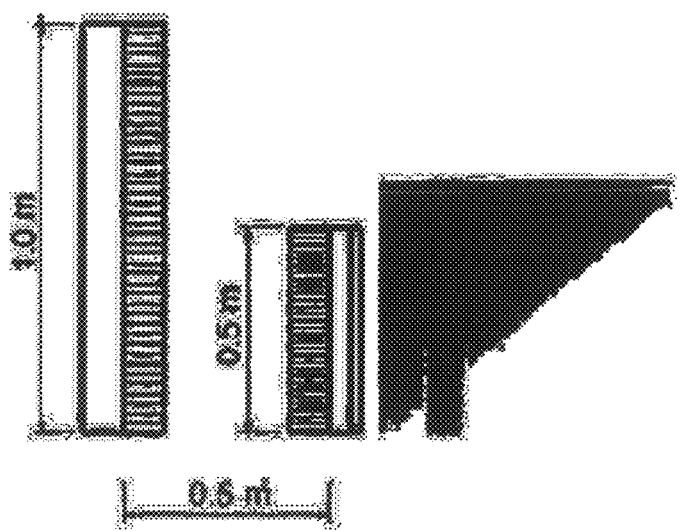

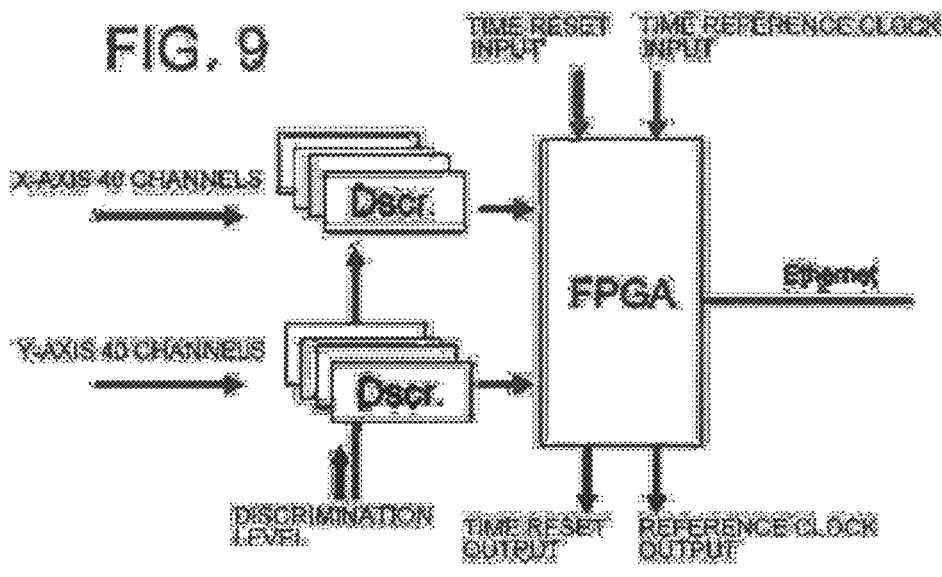
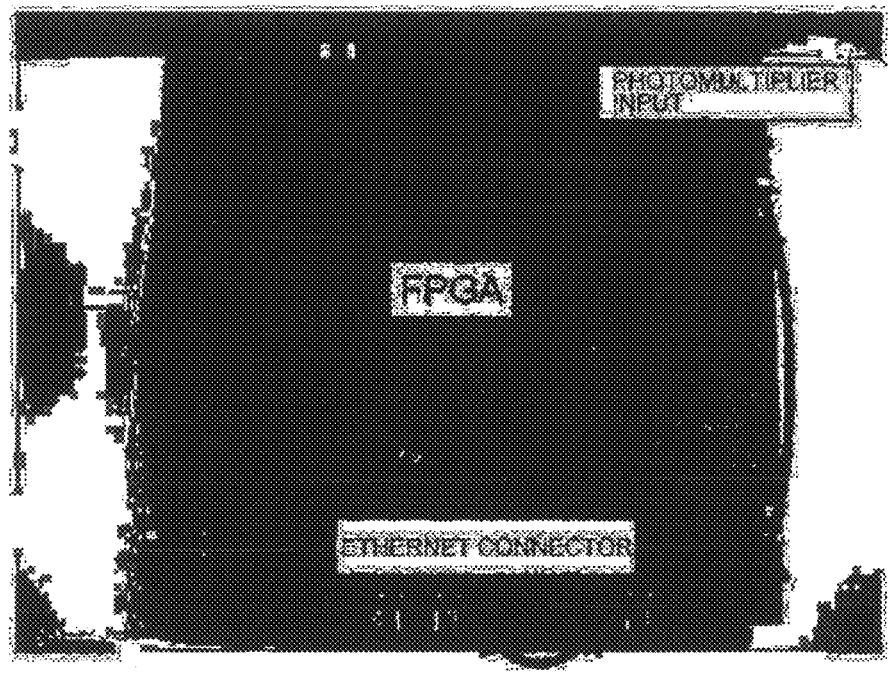
FIG. 9

NONDESTRUCTIVE INSPECTION APPARATUS AND NONDESTRUCTIVE INSPECTION METHOD FOR COMPOSITE STRUCTURE

RELATED APPLICATIONS

The present application is National Phase of International Application No. PCT/JP2009/053140 filed Feb. 23, 2009, and claims priority from, Japanese Application No. 2008-043595 filed Feb. 25, 2008, the disclosure of which is hereby incorporated by reference herein in its entirety.

TECHNICAL FIELD

The present invention relates to a nondestructive inspection apparatus and nondestructive inspection method for enabling a state of the inside of a composite structure such as, for example, a reinforced concrete construction to be inspected without exerting any adverse effect on the structure.

BACKGROUND ART

For example, as a nondestructive inspection method for inspecting or detecting an interior state (non-woven state of the reinforcing bar, etc.) inside a composite structure such as a reinforced concrete construction such as a building, pier of a express highway and dam, or a state inside the surface layer such as iron components and temperature distribution inside a blast furnace, without exerting physical and/or chemical adverse effects on the subject of inspection, there have conventionally been known an ultrasonic method, IR thermography method, radar method, X-ray method, etc. However, all of these methods are limited remarkably in the subject of inspection, while having the limitations in the resolution of the interior state and in the depth inside the surface layer that can be inspected.

Therefore, the inventors and others of the present invention proposed a nondestructive inspection method and apparatus for artificially generating muon particles using a particle accelerator, capturing the muon particles generated with the particle accelerator at a predetermined solid angle while performing magnetic confinement, transporting the particles to inspection targeted reinforced concrete to apply, detecting an amount of positrons emitted by energy loss of the applied positive muons in the reinforcing bar portion, and thereby detecting a state inside the reinforced concrete (for example, see Patent Document 1).

Patent Document 1: Japanese Laid-Open Patent Publication No. 2008-14816

DISCLOSURE OF INVENTION

Problems to be solved by the Invention

However, in the invention as described in Patent Document 1, muon particles are generated using a large expensive particle accelerator, thus artificially generated positive muon particles are captured at a predetermined solid angle while being subjected to magnetic confinement, transported to inspection targeted reinforced concrete and applied, and there is a significant problem in actual implementation possibility. Further, details are not shown on specific data processing of an output signal from a positron detecting means (plastic scintillator) as described in Patent Document 1, and it is difficult in the conventional technique to actually process a detection signal of selected positron/electron amount produced by decay of muons and generate desired radiography information. Furthermore, in the invention as described in Patent Document 1, only positive muons are considered as muon particles, it is not considered to acquire a signal of element selection from negative muons, and therefore, it is not easy to acquire detailed sophisticated data for specific radiography of a shape, dimensions, etc. of a steel rod inside a composite structure.

Means for Solving the Problem

The present invention was made in view of the above-mentioned problems, and provides a nondestructive inspection apparatus for a composite structure which is a nondestructive inspection apparatus for inspecting the inside of the surface layer of a composite structure using cosmic-ray muons incoming mostly in the horizontal direction with spin polarized by a given amount along the incoming direction, and is characterized by the detection of a positron/electron amount emitted with a characteristic time constant in the direction opposite to the incoming direction of the cosmic-ray muons by the decay of the cosmic-ray muons stopping inside the composite structure, and radiography data processing means by the data of the second substance being different from the first substance in the surface layer of the composite structure, as radiography output, from the positron/electron amount detected in the positron/electron detecting means.

Herein, the cosmic-ray muons include positive muons and negative muons, and the positive muons are spin polarized by approximately 30% with respect to the incoming direction.

Then, the positron/electron amount detecting means detects intensity of decay electron/positron up to 50 MeV produced by the decay of the cosmic-ray muons. Therefore, the positron/electron detecting means is comprised of the first detecting plate disposed on the incoming side of the cosmic-ray muons to detect a position and a path of the muons, and the second detecting plate disposed between the first detecting plate and the composite structure to detect a positron/electron amount produced by the decay of the muons stopping inside the composite structure.

Then, it is a feature that the first detecting plate has a position resolution of ±2.50 cm and a sensitive area of 1 m×1 m, and that the second detecting plate has a position resolution of ±1.25 cm and a sensitive area of 0.5 m×0.5 m.

Further, the radiography data processing means is comprised of a discriminator means for sampling an input signal from the positron/electron amount detecting means at a predetermined reference clock, removing a noise component from the sampled input signal, and selecting only detection signals of muons, and a data processing means for processing an output signal from the discriminator means to generate radiography information.

Then, it is another feature that the composite structure is reinforced concrete, the first substance is concrete, the second substance is a steel rod or steel frame, and that in the reinforced concrete, the steel rod or steel frame is in a position a distance ranging from 10 cm to 20 cm from a surface of the concrete.

The invention further provides a nondestructive inspection method which is a nondestructive inspection method for inspecting the inside of the surface layer of a composite structure using cosmic-ray muons incoming substantially in the horizontal direction while being spin polarized by a given amount in the incoming direction, has a step (a) of sampling, at a predetermined reference clock, a positron/electron amount reflection-emitted having a characteristic time constant in the direction opposite to the incoming direction of the muons with annihilation of the cosmic-ray muons stopping inside the composite structure, a step (b) of removing a noise component from the sampled signal, a step (c) of screening detection signals of muons from the signal with the noise component removed, and a step (d) of processing the selected detection signals of muons to generate radiography information, and is to inspect the inside of the composite structure by obtaining the radiography information indicating a state of the second substance different from the first substance of the surface layer existing inside the surface layer of the composite structure.

Herein, the cosmic-ray muons include positive muons and negative muons, and are spin polarized by approximately 30% with respect to the incoming direction.

Advantageous Effect of the Invention

By this means of the non-destructive inspection apparatus and method, since cosmic-ray muons are used, it is possible to perform inspection on any objects at any places. Further, the need of a large expensive particle accelerator is excluded, and the uses of magnetic confinement transport means for capturing muon particles generated by the particle accelerator at a predetermined solid angle while performing magnetic confinement, and transporting to a subject of inspection are not necessary and it is thereby possible to perform nondestructive inspection of a composite structure at low cost.

Further, in the invention, it is possible to accurately detect all the positron/electron amounts produced by the decay of muons including positive muons and negative muons detected in the positron/electron amount detecting means, and it is thereby made possible to acquire detailed sophisticated data for specific radiography display of a shape, dimensions, etc. of a steel rod inside a composite structure. Particularly, it is made possible to measure in a short time the specific information such as a shape, dimensions and corrosion of a steel rod positioned inside the surface layer of a reinforced concrete construction such that that the covering depth ranges from 10 cm to 20 cm in the entire reinforced concrete of 1 m or more thick.

BRIEF DESCRIPTION OF DRAWINGS

FIG. 8 is to explain a segmented plastic counter array for positron/electron amount detecting apparatus constituting the invention;

FIG. 9 shows a block diagram (upper view) of a Read-Out-Module (ROM) circuit (reference numeral "15" in FIG. 1) and a unit photograph (lower view);

DESCRIPTION OF SYMBOLS

11: Composite structure (reinforced concrete)
12: Cosmic-ray muons
13: Positron/electron amount detecting apparatus
14: Discriminator
15: ROM circuit for processing an output signal from the discriminator 14
16: Data processing apparatus (personal computer)

BEST MODE FOR CARRYING OUT THE INVENTION

Described below are the details of a nondestructive inspection apparatus and inspection method for a composite structure using cosmic-ray muons according to the invention.

Figure 1:
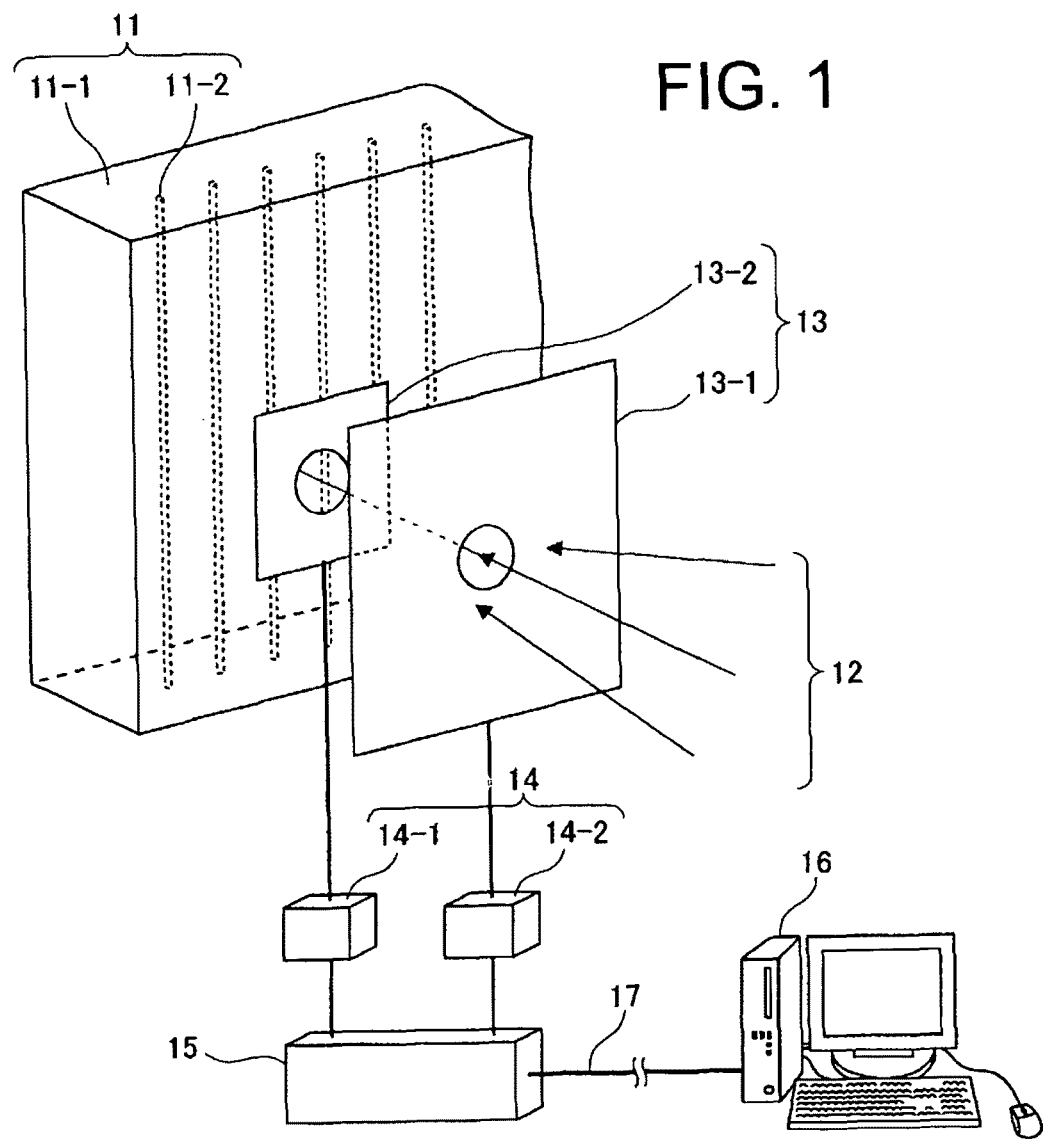
FIG. 1 shows an outline of the entire configuration of a nondestructive inspection apparatus for a composite structure portion of the invention.

FIG. 1 shows an outline of the entire configuration of a nondestructive inspection apparatus for a composite structure portion of the invention. In the nondestructive inspection apparatus of the invention, it is a particular feature using cosmic-ray muons 12 incoming substantially in the horizontal direction while being spin polarized by a given amount in the incoming direction. Then, the invention is to inspect the inside of the surface layer of the composite structure using the cosmic-ray muons.

In FIG. 1, a composite structure 11 targeted for the nondestructive inspection is reinforced concrete 11 comprised of concrete 11-1 that is a surface layer portion, and interior steel rods (or steel frames) 11-2.

As shown in FIG. 1, the nondestructive inspection apparatus of the invention is comprised of positron/election amount detecting means 13 for detecting a positron/electron amount reflection-emitted in the direction opposite to the incoming direction of cosmic-ray muons by the decay of the cosmic-ray muons after stopping inside the composite structure made of concrete and steel rod or steel frame 11-2, and radiography data processing means 14, 15 and 16 for data-processing, as radiography data output, where for example, a corrosion state of the steel rod or steel frame 11-2 (second substance) existing inside the concrete 11-1 (first substance) in a surface layer of the reinforced concrete 11 of the composite structure can be monitored from the positron/electron amount detected in the positron/electron amount detecting means 13.

Herein, the cosmic-ray muons 12 include positive muons and negative muons in the case of the invention, and the positive muons are spin polarized by 30% along the incoming direction.

Then, the positron/electron detecting means 13 (13-1 and 13-2) detects the intensity of decay electron/positron up to 50 MeV produced by the decay of the stopping cosmic-ray muons 12. Therefore, the positron/electron amount detecting means 13 is comprised of the first detecting plate 13-1 disposed on the incoming side of the cosmic-ray muons 12 to detect a position and a path of cosmic-ray muons to irradiate the composite structure 11 targeted for measurement, and second detecting plate 13-2 disposed between the first detecting plate 13-1 and the reinforced concrete 11 that is the composite structure to detect a positron amount and electron amount (in the invention, referred to as "positron/electron amount") produced by the decay of the stopping cosmic-ray muons 12 in the steel rod or steel frame 11-2 existing inside the concrete 11-1 that is the surface layer.

Herein, in the first detecting plate 13-1, as an example, the position resolution is ±2.50 cm, and the sensitive area is 1 m×1 m. Meanwhile, in the second detecting plate 13-2, the position resolution is ±1.25 cm, and the sensitive area is 0.5 m×0.5 m.

Further, the radiography data processing means 14, 15 and 16 is comprised of a discriminator 14 (14-1, 14-2) for sampling an input signal from the positron/electron amount detecting means 13 at a predetermined reference clock, removing a noise component from the sampled input signal, and selecting only detection signals of muons, a ROM circuit (Read-Out Module Circuit) 15 for processing an output signal from the discriminator 14 (14-1, 14-2), and a data processing means (for example, personal computer) 16 connected to the ROM circuit 15 via an indoor communication channel (LAN) such as Ethernet.

Herein, in the invention, in the reinforced concrete 11 that is the composite structure targeted for nondestructive inspection using the cosmic-ray muons 12, it is possible to sufficiently measure the steel rod or steel frame 11-2 at a distance in the range of 10 cm to 20 cm from the surface of the concrete 11.

Each above-mentioned configuration constituting the above-mentioned nondestructive inspection apparatus of the invention will specifically be described below.

A. Description of Muons

Described first is the outline of a muon (hereinafter, referred to as "μ" as appropriate) used in the invention.

The muon is an elementary particle having a mass about one/ninth of the mass of a proton or about 207 times the mass of an electron, and there are two kinds of muons, $\mu^+$, $\mu^-$, respectively having positive and negative charges. $\mu^+$ and $\mu^-$ in vacuum decay with a lifetime of 2.2 μs, and in decay, produce positron $e^+$, electron $e^-$ and neutrino with energy up to 50 MeV. Although the muons reach the earth's surface as cosmic rays, to obtain muons with high intensity, protons and electrons with high energy are used via a particle accelerator, pions (Yukawa mesons, $\pi^+$, $\pi^-$) are produced by reaction with the atomic nucleus, and it is possible to produce a large amount of $\mu^+$ and $\mu^-$ by decay of pions. For the muon stopping in a substance, only electromagnetic interaction mainly works. Using the property of elementary-particle muon, it is possible to apply to various practical fields, and in the invention, it is a feature using cosmic-ray muons, instead of muons artificially produced by such a particle accelerator.

The cosmic-ray muons have almost common energy spectra at any place at any time once the zenith angle is selected. Accordingly, by measuring intensity attenuation in passing through a substance with an unknown (thickness) (density×length), it is possible to measure the "thickness". In the intensity attenuation measurement, using two or more position sensitive detectors (positron/electron amount detecting apparatus 13: the first detecting plate 13-1 and the second detecting plate 13-2), the intensity attenuation is obtained sequentially for every path of muons after passing through the substance under inspection, and it is thereby possible to obtain a mapping of spatial distribution of the "thickness" inside the substance. At this point, the feature of the mass of the muon is 200 times heavier than the mass of the electron and the feature that only the electromagnetic interaction works are most effectively working. Thus, the muons with high energy, thereby penetrate, for example, up to several kilometers in a rock or up to 100 m in iron, and can be a subject of radiography. Muons having such high energy can be obtained as cosmic rays that are environmental radiation. The invention uses such cosmic-ray muons.

B. Principles of Reflection Cosmic-Ray Muon Radiography

In transmission radiography, it is necessary to install a detector after the substance under investigation along the incoming direction of cosmic rays. There are cases that such an arrangement is not made in an existing large construction, a pier of an elevated road, etc. In this case, it is only permitted to obtain a reflection signal to explore the inside. Therefore, reflection signals by horizontal cosmic-ray muons are used in the nondestructive inspection according to the invention.

C. Detection of Positron/Electron Amount by μSR Method

The μSR method is a method for measuring the magnetic field inside a substance using magnetic moment that muons have as a microscopic magnetic needle. Positive muons are 60% of cosmic-ray muons and are spin polarized by about 30% with respect to the incoming direction. By this means, the μSR signal enables composition analysis of an object deep portion. Further, in the invention, as well as positive muons, element selective signals from negative muons are considered and it is thereby possible to acquire detailed data for specific radiography of the shape, dimensions, etc. of a steel rod inside the composite structure.

The positron having energy up to 50 MeV produced by decay of $\mu^+$ polarized in spin in the incoming direction is emitted in the direction of polarized spin. Then, by detecting the positron, it is possible to probe the microscopic magnetic property of the substance (μSR method). By applying the technique of the μSR method implemented in this way, it is possible to observe minute static and dynamic magnetic fields with high sensitivity.

Figure 2:
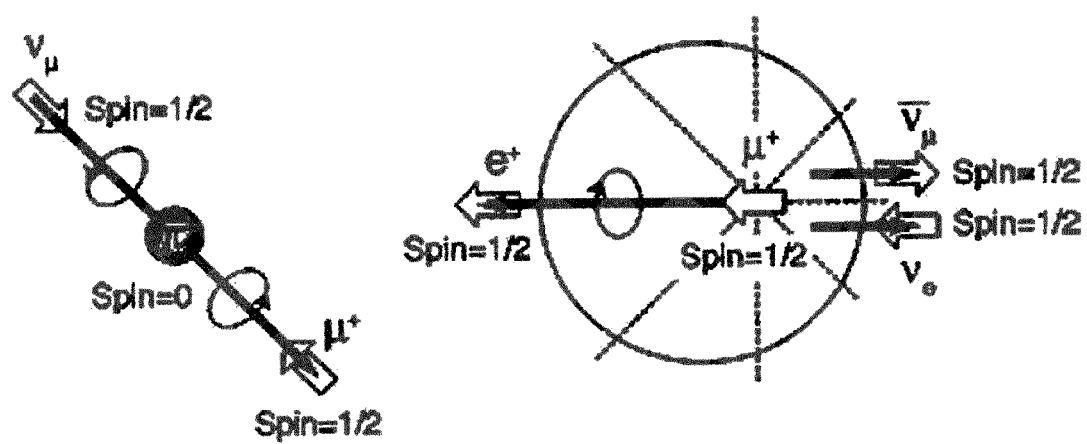
FIG. 2 shows a principle diagram of a muon spin rotation (μSR) method used in the invention, where the left diagram in FIG. 2 shows production of a spin polarized muon from pion decay, and the right diagram in FIG. 2 shows production of a positron from the spin polarized muon with spatial asymmetry.

FIG. 2 shows a principle diagram of the aforementioned μSR method. Herein, the left diagram in FIG. 2 shows production of a spin polarized muon from pion decay, and the right diagram in FIG. 2 shows production of a positron from the spin polarized muon with spatial asymmetry.

Figure 3:
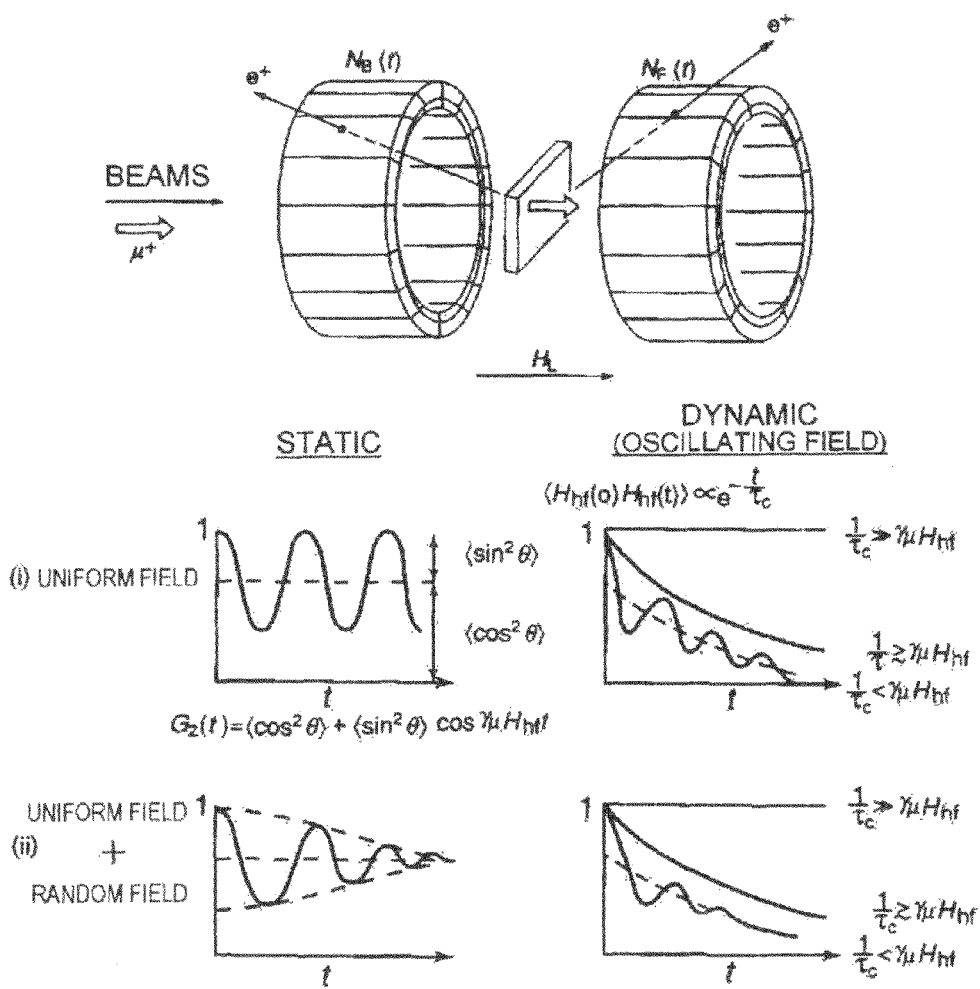
FIG. 3 shows a conceptual diagram (upper diagram) of a μSR measurement apparatus, and (lower diagram) a typical example of correspondence between the observed μSR signal and microscopic magnetic field where the external magnetic field is zero.

Further, FIG. 3 shows a conceptual diagram (upper diagram) of a μSR measurement apparatus, and (lower diagram) a typical example of correspondence between the observed μSR signal and microscopic magnetic field where the external magnetic field is zero where the external magnetic field is zero. By using this μSR method, it is possible to acquire an existence state of a steel rod or reinforcing bar inside the concrete easily and precisely.

Figure 4:
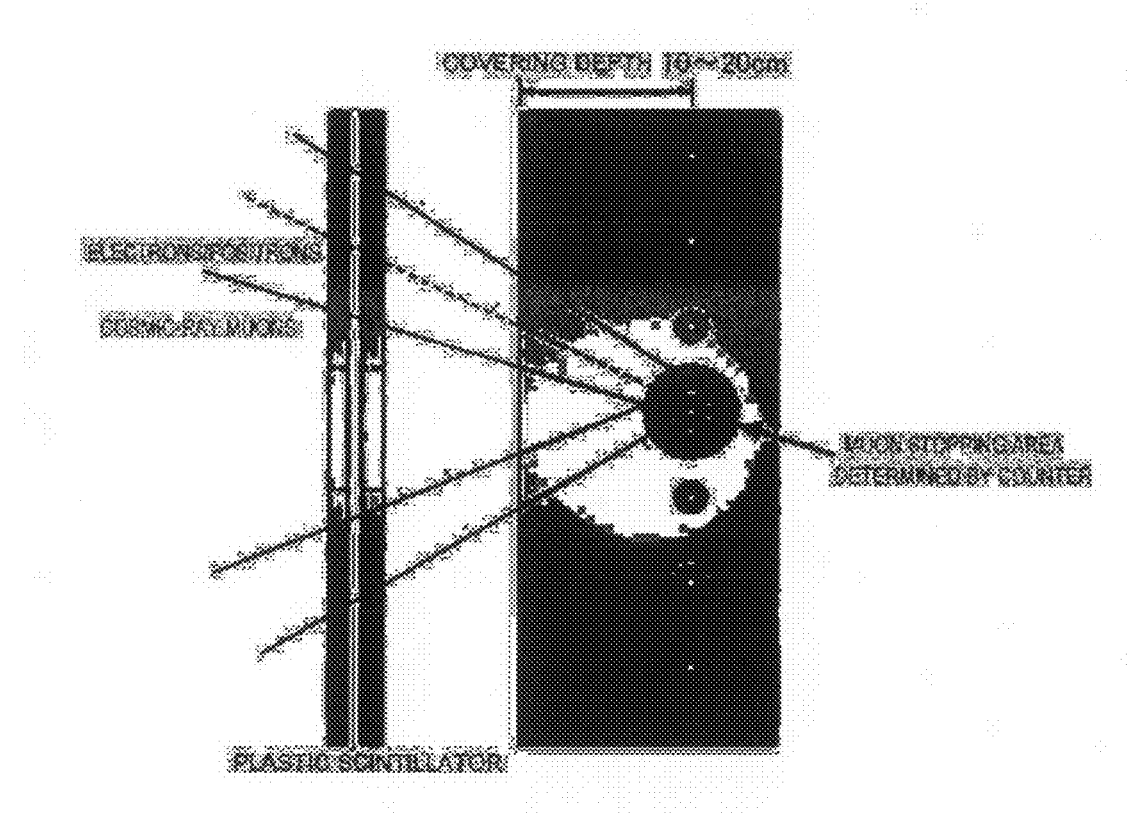
FIG. 4 illustrates a state where cosmic-ray muons are stopped inside reinforced concrete, the intensity of emitted positrons/electrons are measured, and an existence state of a steel rod is inspected by the μSR method.

FIG. 4 illustrates a state where cosmic-ray muons are stopped inside reinforced concrete, the intensity of emitted positrons is measured, and an existence state of a steel rod is inspected by the μSR method. The spin of muons stopping in the concrete has a weak relaxation phenomenon due to magnetic impurities, etc. and is as shown in the upper right diagram in FIG. 3. When muons stop at iron, by the internal magnetic field, rapid spin rotation of about 50 MHz occurs. Then, when the time resolution in the measurement system is lower than 20 nanoseconds, the rotation is invisible and the detected positron intensity becomes one third. Accordingly, for example, by arranging the measurement device as shown in FIG. 4, when muons stop at iron, decreases in the positron intensity occur. Therefore, by measuring the positron intensity as a function of the position of the beams, it is possible to measure the arrangement and thickness of the steel rod inside the reinforced concrete distinctly in a short time.

D. Muon Nuclear Absorption Electronic Signal

In the invention, as well as positive muons, decay of negative muons is the subject of inspection. Using negative muons occupying 40% of cosmic-ray muons as the subject of inspection, it is possible to obtain a reflection signal specific to the substance as described below. The negative muon stopping inside the substance decreases the velocity, becomes a small atom rotating about the atomic nucleus of the substance, and after atomic transition, reaches the ground state of the atom. In the ground state, overlapping with the atomic nucleus increases corresponding to the increase of the charge Z of the atomic nucleus, and the negative muon is captured into the atomic nucleus. As a result, the probability of free decay of muons varies with the charge Z. The probability is 50% in the concrete, and 10% in iron. Accordingly, attenuation occurs in the intensity of decay electron/positron up to 50 MeV appearing as a reflection signal when the muon stops at iron.

Figure 5:
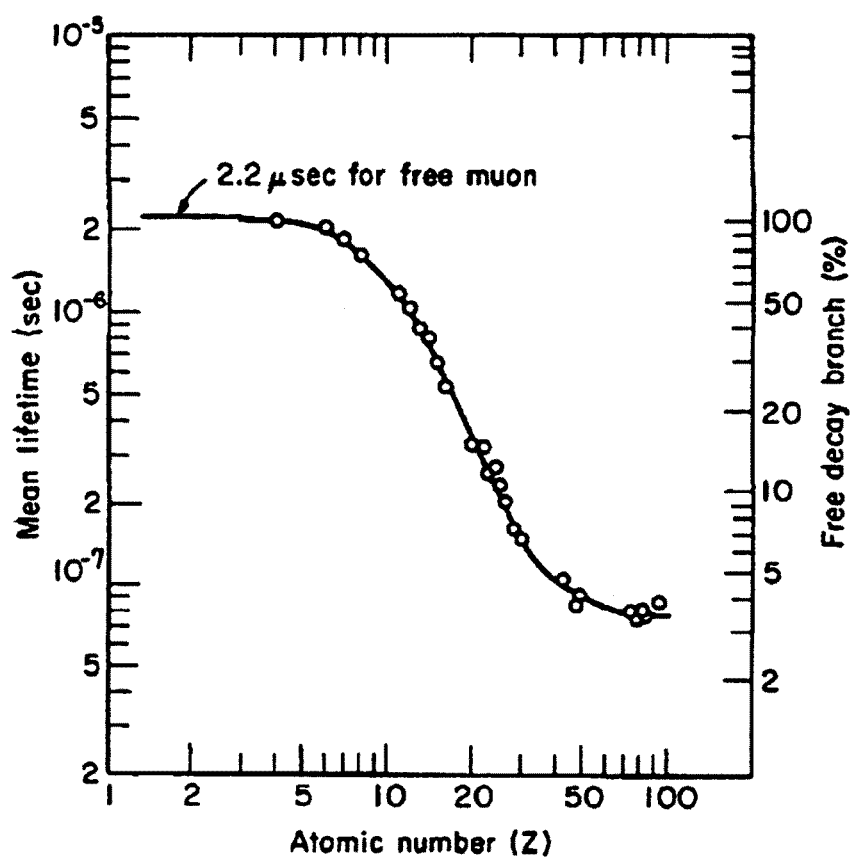
FIG. 5 shows variations in capture rate of a negative muon into an atomic nucleus and probability of free decay with charge Z of the atomic nucleus.

FIG. 5 shows variations in capture rate of a negative muon into an atomic nucleus and probability of free decay with charge Z of the nucleus.

E. Description of the Reflection Signal of Cosmic-Ray Muon

Figure 6:
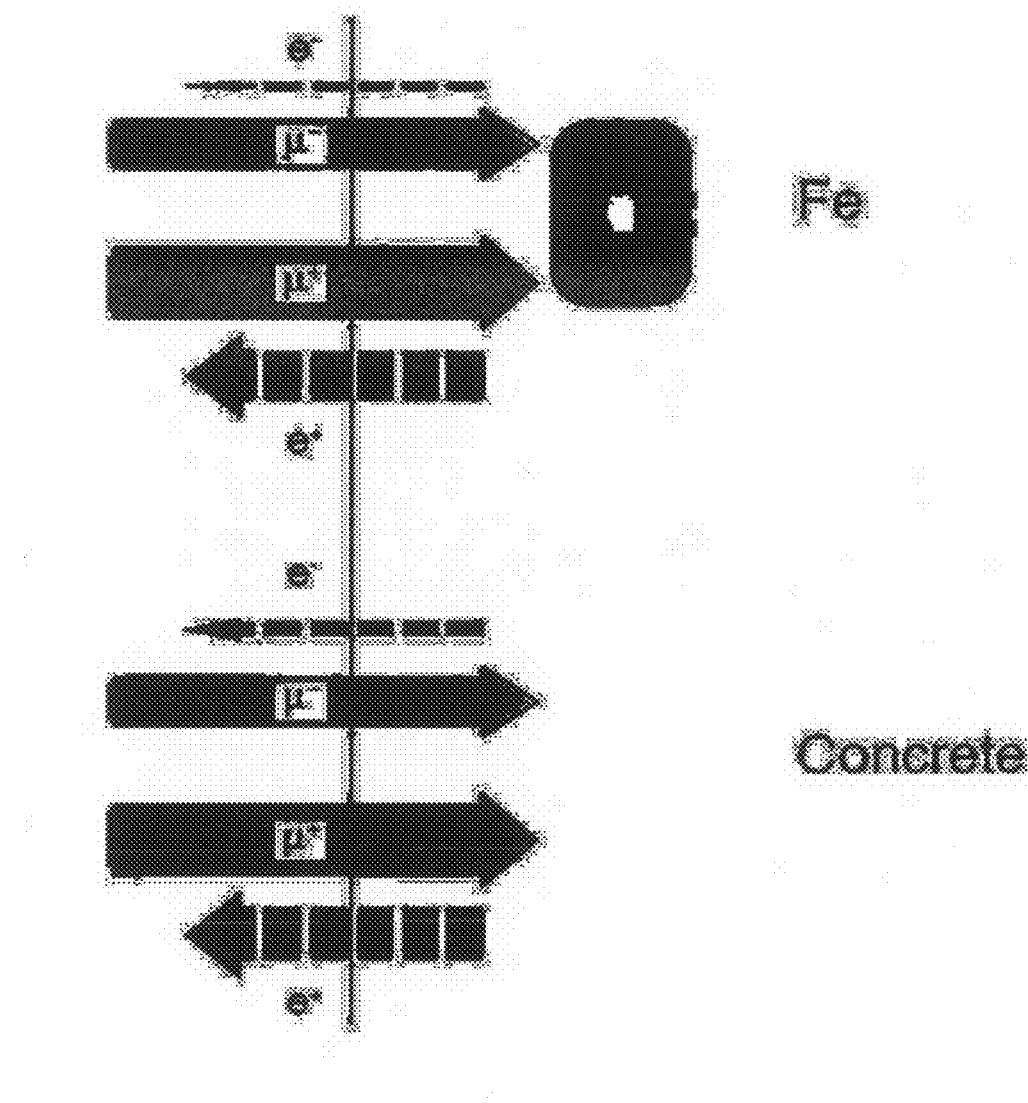
FIG. 6 shows reflection signals generated by cosmic-ray muons, and shows that the total intensity of positron and electron reduces by 17% in stopping at iron as compared with the case at concrete.

As described above specifically, by detecting intensity of the high energy positron/electron obtained as a reflection signal using cosmic-ray muons incoming along the horizontal direction to stop inside the object like as shown in FIG. 6, it is understood that the following change occurs in the case that the muon stops at iron, as compared with the case of stopping at the concrete.

Generally, the intensity $N_e(T)$ of decay positron/electron from a stopping muon is expressed as described below. In other words:

$$N_e(T) = \alpha N_\mu e^{-T/\tau_\mu}(1 + A_\mu P_\mu \cos \omega T)\Delta\Omega$$

wherein $N_\mu$; intensity of cosmic-ray muon, $\alpha$; intensity ratio between positive and negative muons, $\tau_\mu$; lifetime of muon, $P_\mu$; degree of polarization of muon, $A_\mu$; asymmetric degree of decay positron/electron, $\omega$; rotation angular velocity of muon spin by atomic internal magnetic field, and $\Delta\Omega$; solid angle of the detector. Then, the above-mentioned intensity $N_e(T)$ of decay positron/electron is integrated with respect to time, and the sum of reflection signals from positive and negative muons is calculated for the concrete and iron.

$$N_e/\Delta\Omega(\text{concrete}) = 0.6 \times 2.2 \times (1 + 0.3 \times 0.3 \times 1) + 0.4 \times 0.9 \times 1$$
$$= 1.44 + 0.30$$
$$= 1.74$$

$$N_e/\Delta\Omega(\text{iron}) = 0.6 \times 2.2 \times (1 + 0.3 \times 0.3 \times 1/3) + 0.4 \times 0.2 \times 1$$
$$= 1.36 + 0.08$$
$$= 1.44$$

The aforementioned calculation processing is performed by the radiography data processing means 14, 15, 16 as shown in FIG. 1.

FIG. 6 shows reflection signals generated by cosmic-ray muons, and shows that the total intensity of positron and electron reduces by 17% in stopping at iron as compared with the concrete. By using this change of 17% to identify a position at which muons stop and using a multiple position sensitive detectors, reflection type radiography of reinforced concrete can be realized. At this point, since the energy of muon decay electron/positron obtained as a signal is 50 MeV, it is possible to investigate reinforced concrete with a concrete thickness ranging from 10 cm to 20 cm, and the covering depth of 10 cm or more.

As a reflection signal, in addition to the signal as described above, it is possible to use negative muon atomic X-ray signal, negative muon nuclear capture neutron, etc. However, in addition to poor efficiency and difficulty to determine the path of the signal, practical use is difficult. There positive muon is not used at all. Furthermore, for detection of a reflection signal of the cosmic-ray muon, it is necessary to detect a single muon and detect the accompanying positron/electron, and it is impossible to employ the nuclear plate method which is entirely without time correlation. Therefore, the technique according to the invention is extremely effective.

F. Description of the Positron/Electron Detecting Apparatus 13

In the positron/electron detecting apparatus 13 used in the invention, the first detecting plate 13-1 has a form such that a set of all the detection systems is accommodated inside a rectangular box of 1 m square with a thickness of 50 cm as a whole, and multiple sets are combined and placed just in contact with the object such as a large construction substance to be investigated, and measurement of the states of steel frames of reinforced concrete with a covering depth ranging from 10 cm to 20 cm with the resolution of ±5 mm will be completed within six months. As the data, the intensity of the reflection signal is related to the actual surface coordinates of the object, portions with low signal intensity correspond to iron portions, and the soundness of the reinforcing bar is evaluated by the structure of this portion. All the data is recorded with absolute time resolution of 10 ns and spatial resolution of 10 mm. Among the measured data, by time and space reconstruction by compiling spatial data considered to be similar and adding and multiplying all of those, it is possible to monitor in a short time the soundness of the construction to be confirmed in long-time measurement.

Figure 7:
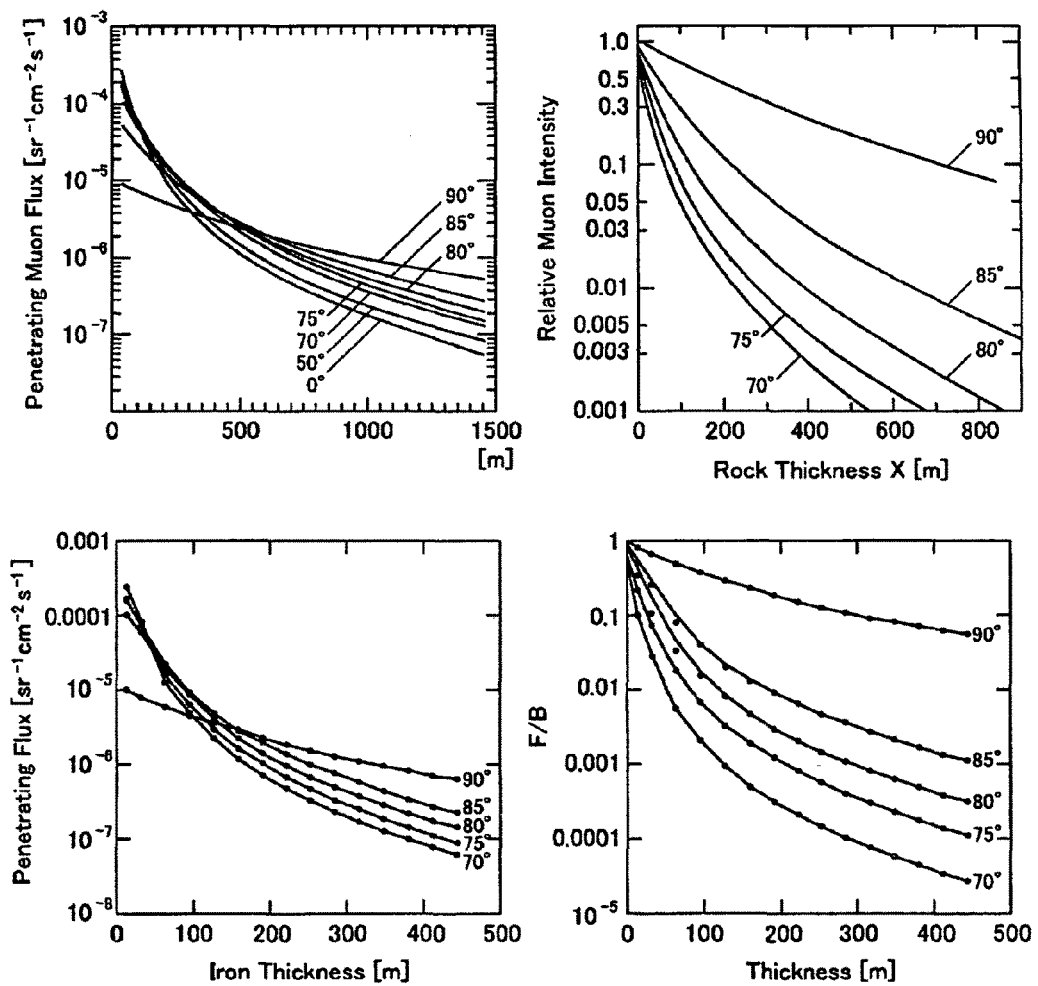
FIG. 7 contains graphs showing the penetrating intensity of cosmic-ray muons at various zenith angles through various thickness of iron (left) and rock (right) and relative intensity normalized by zero thickness is shown in the right side.

Described herein is required measurement time. It is known that the intensity of cosmic-ray muons at a zenith angle of 70 degrees is $0.001/(\text{sTr})/(\text{cm})^2/\text{s}$ as shown in FIG. 7. Among them, 2% stops at concrete with a thickness of 10 cm. Accordingly, the muon intensity is as follows corresponding to the (maximum incident area and spreading in the position with the covering depth of 10 cm) of incident muon defined by a front cosmic-ray muon counter: 10/day (1 m×1 m, 5 cm×5 cm), 0.1/day (10 cm×10 cm, 5 mm×10 mm).

Since the solid angle of muon decay positron/electron changes to 0.12 and 0.0012, the detection amount of decay positron/electron obtained as a reflection signal is as follows corresponding to the spatial resolution in the position with the covering depth of 10 cm: 0.12/day (5 cm×5 cm, 5 cm×5 cm), 0.1/day (10 cm×10 cm, 5 mm×10 mm). Accordingly, since the solid angle of muon decay positron/electron changes to 0.12 and 0.0012, the reflection signal detection is as follows corresponding to the spatial resolution: 0.12/day (5 cm×5 cm), 0.00012/day (5 mm×5 mm). As described previously, there is a difference of 17% in the intensity of positron/ electron amount between the case of stopping at the concrete and the case of stopping at iron. From these considerations, to identify iron inside the concrete by the proposed cosmic-ray muon reflection radiography method, it takes three months with a resolution of centimeters, while taking ten years with a resolution of millimeters.

From the aforementioned consideration, the reflection cosmic-ray muon radiography method in the invention may be misunderstood as having the limitations due to long measurement time. In other words, even when the apparatus is enlarged, the targeted area is enlarged, and to obtain the same spatial resolution, the same long-time measurement is required. However, the technique overcoming the limitations is the time and space reconstruct ion method by high-speed electronic circuit ROM for cosmic-ray muon radiography as described later. It is possible to determine and record the passing position and direction of cosmic-ray muons with accuracy of the position sensitive detector, and the absolute time of the event with accuracy of 10 ns. Accordingly, after acquiring the data, the data is compiled in the appropriate time domain and space domain, the accuracy of the data is effectively increased, and it is possible to obtain the accuracy of the order of millimeters in targeted six months.

G. Description of the Detector System

FIG. 8 is to explain principles of the positron/electron amount detecting apparatus 13 in the invention. To know the position and path of cosmic-ray muons, the incident side F counter (the first detecting plate) has a thickness of 3 cm, position resolution of ±2.5 cm, and sensitive area of 1 m×1 m, the object side B counter (the second detecting plate) has a thickness of 1.5 cm, ±1.25 cm, and 0.5 m×0.5 m, the distance between F and B is set at 0.5 m, and nearly horizontal cosmic rays are used such that the zenith angle ranges from 45 degrees to 90 degrees. It is assumed that the detection of reflection electron/positron intensity is made by the object side counter B, and to use the ROM circuit 15 effectively, a trigger counter T with a thickness of 0.5 cm and 0.5 m×0.5 m may be disposed immediately before the object. By this means, it is possible to select muons with excellent linearity, bring the counter intimate contact with the object, and to image the reinforcing bar placed in the covering depth of 10 cm or more in the targeted reinforced concrete with accuracy of 10 mm or more by interpolating the acquired data, and the like.

In FIG. 8, it is defined that the incident side F counter to determine the path and position of cosmic rays has a thickness of 3 cm, position resolution of ±2.5 cm, and sensitive area of 1 m×1 m, the object side B counter has a thickness of 1.5 cm, position resolution of ±2.5 cm, and sensitive area of 0.5 m×0.5 m, and that the distance between F and B is 0.5 m. It is assumed that the object side counter B performs reflection electron/positron signal detection, and to effectively use the ROM circuit system, the trigger counter T with a thickness of 0.5 cm and 0.5 m×0.5 m is provided immediately before the object. The counter is brought into intimate contact with the object, and it is possible to image the reinforcing bar placed in the covering depth of 10 cm or more in the targeted reinforced concrete with accuracy of 10 mm by interpolating the acquired data, and the like.

H. Description of the Time Space Reconstruction Method and ROM Circuit

Figure 11:
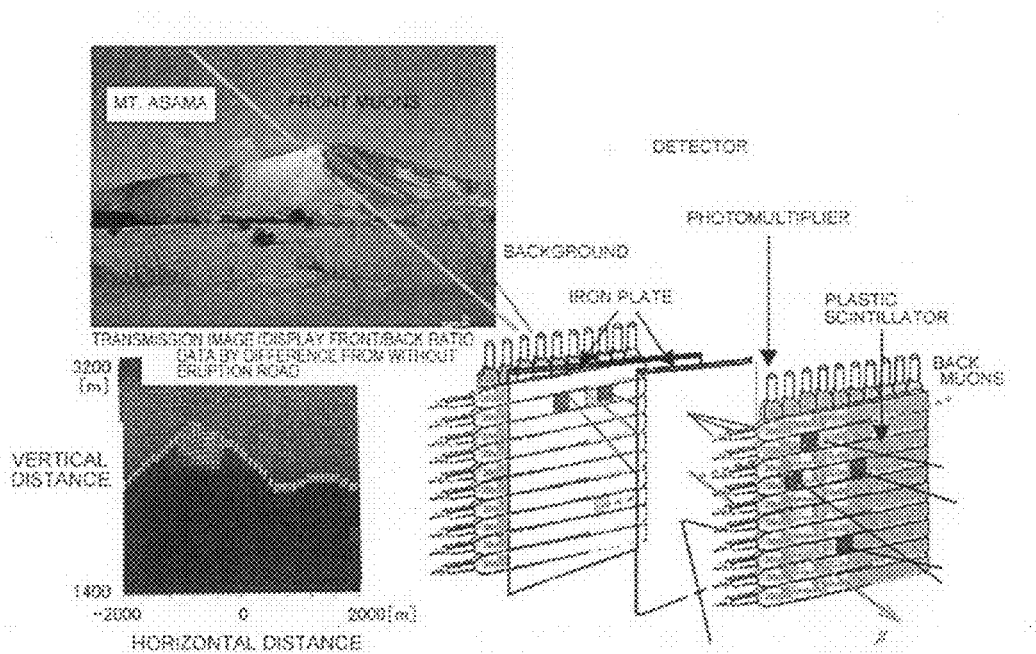
FIG. 11 shows a cosmic-ray muon transmission radiography measurement apparatus for observation of a transmission image of the top of the volcanic mountain and the measurement results.

A universal circuit system data read-out module (Read-Out Module, ROM) developed for muon radiography experiments is capable of processing outputs of a maximum of 40×40 (x axis×y axis) intersecting scintillators (photomultipliers) as shown in FIG. 11, and detecting a point which a muon passes through, and determines track of the muon using two sets of 40×40 scintillators.

FIG. 9 shows a block (upper diagram) of a read-out board, and unit photograph (lower view). Outputs of photomultipliers on the X and y axes are connected to the discriminator, and an output signal of the discriminator is sampled at a time reference clock (100 MHz). Next, a pass point is determined from the sampled photomultiplier input. For the pass point, shower components are removed while considering only a single output of each of x and y axes scintillators effective, and only cosmic-ray muons are screened. When the point is judged to be a muon pass point, the detected result is transferred to the PC via Ethernet, and the data transferred to the PC is comprised of following three items H. Herein, as the time, the absolute time is described with accuracy of 10 ns, and indicates the x axis scintillator number and y axis scintillator number.

In the detection system of the invention, by using two above-mentioned ROM boards, the data obtained in the detector system is to give a knowledge of the pass position and absolute time $(x1, y1, T_\mu), B(x2, y2, T_\mu)$ of the muon at the front and back counters of the cosmic-ray muon with soft-component cosmic-ray background removed, and to give a knowledge of the position, path and incoming time with accuracy of 10 ns of the cosmic-ray muon. In addition, the back countermeasures $F(x', y', T_e)$ of the electron/positron up to 50 MeV emitted from the muon penetrating and stopping at the object, and the distribution of $(T_e-T_\mu)$ is obtained from a function of the position inside the object determined by (x1, y1, x2, y2, x', y'). A reflection signal is confirmed from the fact that the time distribution is in agreement with the muon decay time constant.

Then, by exploiting generality of this measurement method, the data is reconstructed temporally and spatially. For example, when statistics of data are short and it is desired to know the whole state of the steel frame, a similar region is added and accumulated by reconstruction of (x1, y1, x2, y2, x', y'), and the data is obtained apparently with accuracy. Further, for a periodically occurring phenomenon, it is possible to compile the data temporally later to analyze.

As specifically described above, the nondestructive inspection method for a composite structure according to the invention has the following features: In other words, (a) Cosmic-ray muons can be used at any time at any place.
(b) Since nearly horizontal cosmic rays are used, measurement is started immediately with the object left as it is.
(c) The method is completely nondestructive for a subject of inspection. In other words, any physical or chemical adverse effect is not exerted on a composite structure that is the subject of inspection.
(d) It is possible to target a reinforcing bar with a covering depth ranging from at least 10 cm to 20 cm from the transmission property of cosmic-ray muon and decay positron/electron.
(e) Monitoring of a lapse of long-time measurement enables time space reconstruction using the universal read-out circuit system.

Therefore, the nondestructive inspection apparatus and method of the invention enable verification of the soundness of large constructions, verification of the soundness of piers of elevated roads and dams, and the like.

As specifically described above, the present invention is to actualize nondestructive inspection of composite structures using reflection radiography of positron/electron amount produced at the time of annihilation of cosmic-ray muons. Meanwhile, it is possible to apply cosmic-ray muons in various manners by using transmission radiography.

Figure 10:
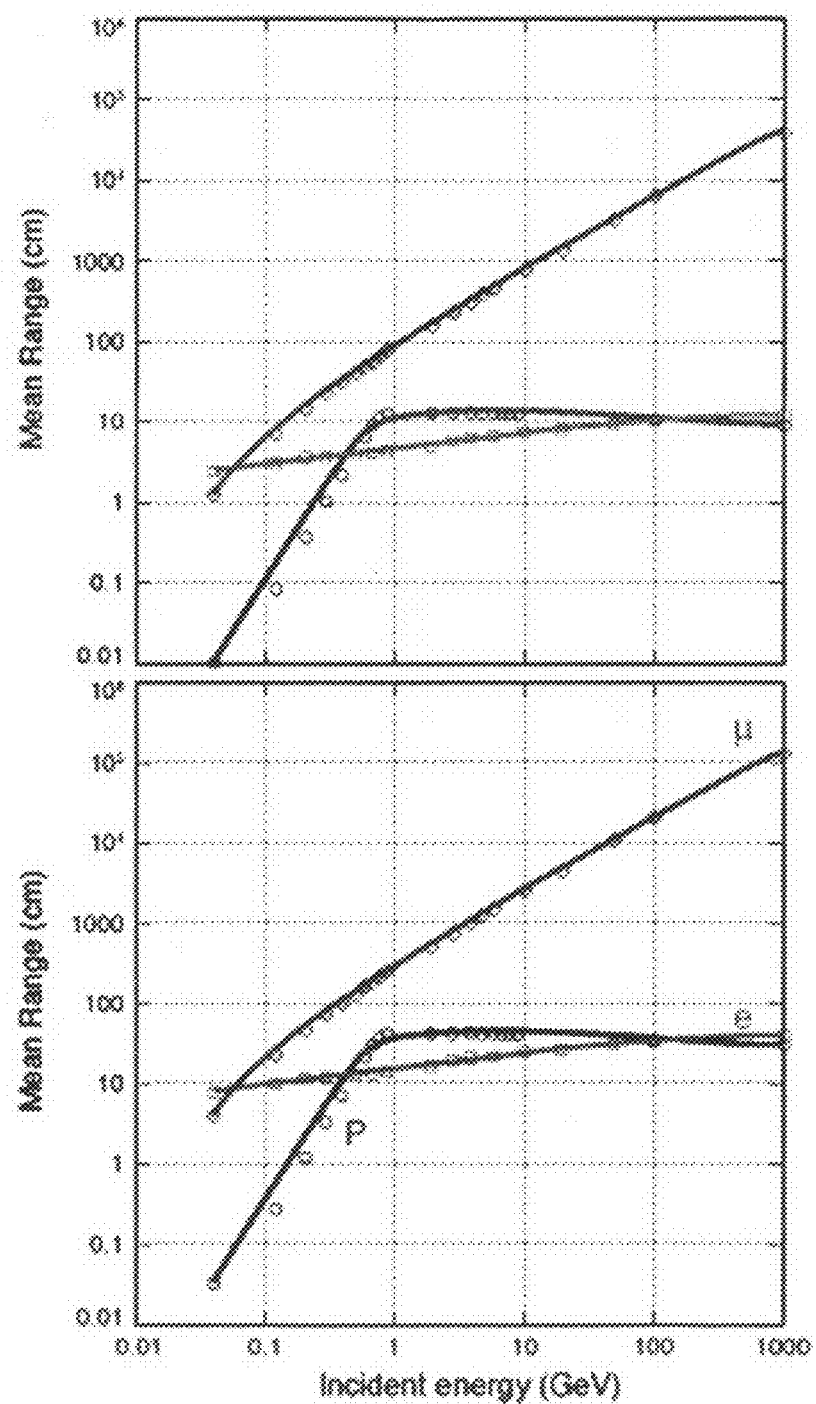
FIG. 10 illustrates that muons penetrating range in iron (upper) and carbon (lower, earth crust, etc. such as a volcanic body and rock) with reference to electron and proton.

H. Principles and Results of Transmission Radiography (1) Principles of Transmission Intensity Attenuation Method As a radiograph is taken to obtain a transmission image of the body using light (X ray), the following items are required to obtain a transmission image: a) The range (penetrating distance in the substance up to stop) with respect to energy of light/particle is longer than or almost equal to the thickness of an object. b) Detection of light/particle is ease and the path is easily identified. As shown in FIG. 10, generally, as the energy of a particle increases, the range of the particle in various substances increases. However, for electrons and protons, even when the energy is increased greatly, the range cannot be increased because of "transform into light due to the light mass" and "increases in nuclear reaction", respectively. In such a case, muons are extremely effective.

FIG. 10 illustrates that cosmic-ray muons penetrate carbon (earth crust, etc. such as a volcanic body and rock).

Further, FIG. 7 shows thickness dependence of transmission intensity of cosmic-ray muons with respect to carbon (upper) and iron (lower). In FIG. 7, the absolute value of transmission intensity is represented on the left, a relative value to a value of thickness of zero corresponding to the F/B ratio is represented on the right, and values associated with various zenith angles are shown. As shown in the figures, the transmission amount in the same thickness varies with a difference in the density.

(2) Application of the transmission intensity attenuation method to volcano/large industrial equipment to actualize radiography display using cosmic-ray muons near the horizontal direction (zenith angles in the range of 60 degrees to 85 degrees), the detection system as shown in FIG. 11 was constructed. As a plurality of position sensitive detectors, plastic scintillators finely divided in grid form are used. Herein, to use muons in the horizontal direction which are good in transmission property but low in intensity, such a scheme was considered that cosmic-ray muons in the opposite direction are simultaneously captured and standardized to obtain the F(the object side)/B(the sky side) ratio. To remove background noise components of a large number of soft components (electrons, gamma rays, etc.) nearly several-ten times than muons, multi-occurring signals produced by soft components due to iron placed at midpoint were used.

Nearly horizontal cosmic-ray muons are good in transmission, settings of experimental conditions are ease, it is possible to measure an object as it is, and it is not necessary to dig a tunnel under a targeted volcanic body, furnace or the like. Further, it is possible to perform tomography observation using a plurality of measurement device systems.

FIG. 11 shows a cosmic-ray muon transmission radiography measurement apparatus, observation of a transmission image of the top of Mt. Asama that is the volcanic body using the apparatus, and the measurement results. There is an aggregate of two 1 m×1 m plastic counters which are partitioned in the vertical and horizontal directions with a width of 10 cm to identify the pass point of muons. By backing the front and back pass points, it is understood where muons pass in the object. Using the iron plate placed at midpoint, soft-component background is removed by "multiple occurrence event removal".

(3) Application to Internal Search of a Volcanic Body

The measurement devices were placed in Onioshidashi Asamaen located 4 km on the north side from the top of Mt. Asama, and it was attempted to observe the crater that cannot be seen from the outside from the outside. Images were taken aiming at the position of the top of Mt. Asama, and a dent became visible which would be the same as the outside shape if all filled. The crater can be seen through from the outside. The data was retrieved for about 100 days, and compared with computer simulations, and the data was obtained in agreement with the fact that the crater is "empty" without magma rising.

Further, as a mechanism of Mt. Iwate volcanic activity, the possibility of "phreatic explosion" has been discussed which is going on along the ridge extending about 4 km in an east-west direction between Mt. Kurokura located 10 km on the west side from the top of Mt. Iwate and Mt. Ubakura. From 2003 to 2004, the measurement devices were set in a position which was located 2.7 km on the north side at a right angle from the ridge between the Mt. Kurokura where volcanic activity is going on and Mt. Ubakura and which was 0.8 km lower than the ridge. The measurement results were compiled, and shown by density length of the cross section of the mountain obtained from the intensity of muons penetrating the mountain, and it is understood that the ridge between Mt. Kurokura and Mt. Ubakura can be considered a mountain structure having the density of 2.5 g/cm$^3$ (±10%) on the premise of uniform density. By comparing with the height of the developed volcanic column in time series analysis of the results, the possibility was pointed out that the cause is freezing of water inside the mountain in winter.

(4) Application to Internal Search of a Blast Furnace

Using the same measurement system as that used in the volcano, furnace walls and furnace bottom of a blast furnace were searched, and for the purpose of searching the internal state and confirming the soundness, experiments were performed in an actual ironworks.

Figure 12:
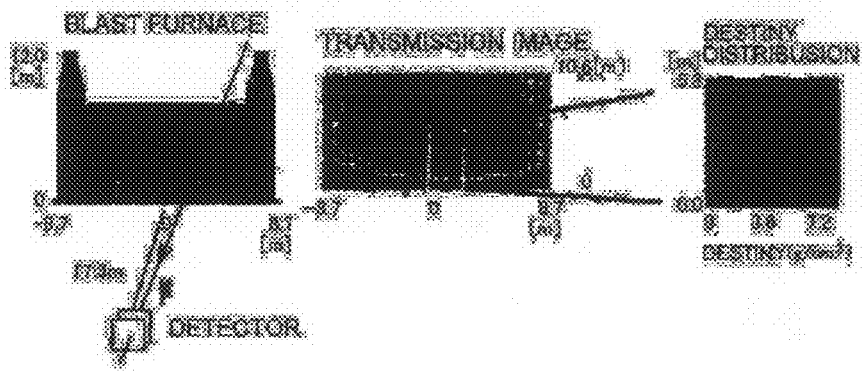
FIG. 12 shows circumstances of inner structure measurement of an operating blast furnace, obtained raw data of relative intensity in F/B ratio (middle), and obtained density distribution (right).

FIG. 12 shows circumstances of measurement in, experiments of an operating blast furnace, obtained raw data of F/B ratio, and obtained density distribution. The F/B ratio in the center position in the lateral direction changes in the upward direction from the bottom, and the difference between the iron portion and the brick portion is recognized. The left diagram in FIG. 12 shows an arrangement of the measurement system of cosmic-ray muon radiography experiments, the center diagram in FIG. 12 shows obtained raw data of F/B ratio, and the right diagram in FIG. 12 shows the density distribution obtained by displaying the level of F/B ratio of cosmic-ray muon intensity by three-dimensional height and color to analyze, with respect to each point of the blast furnace determined by up, down, right and left angles (mrad) to observe the blast furnace. The following matters are found:

(a) The determination accuracy in measuring the brick thickness of the furnace bottom portion or furnace wall portion is ±5 cm/45 days, assuming the cylindrical symmetry of the furnace in analysis. This enables estimation of life of a blast furnace which would be 20 years to be performed by two-month measurement with accuracy of several months.

(b) Determination of the iron density shows ±0.2 g/cm$^3$ by measurement for two months with respect to the 50 cm×50 cm partitioned cross section.

(c) It is possible to monitor time/space variations of conditions of iron inside the furnace to some extent, and spatial variations of the iron portion due to the effect of shutdown were observed.

INDUSTRIAL APPLICABILITY

The present invention relates to a nondestructive inspection apparatus and inspection method thereof for enabling a state of the inside of a composite structure such as, for example, a reinforced concrete construction to be inspected without exerting any adverse effect on the structure using cosmic-ray muons, and has industrial applicability.

The invention claimed is:

1. A nondestructive inspection apparatus for inspecting an inside of a surface layer of a composite structure using cosmic-ray muons incoming substantially in a horizontal direction with being spin polarized by a given amount in a incoming direction, the apparatus comprising:
positron/electron amount detecting means for detecting a positron/electron amount reflection-emitted having a characteristic time constant in a direction opposite to the incoming direction of the cosmic-ray muons by a decay of the cosmic-ray muons stopping inside the composite structure; and
radiography data processing means for monitoring a state of a second substance, different from a first substance of the surface layer, existing inside the surface layer of the composite structure, as radiography to output, from the positron/electron amount detected in the positron/electron detecting means,
wherein the positron/electron amount detecting means comprises
a first detecting plate disposed on an incoming side of the cosmic-ray muons to detect a position and a path of the cosmic-ray muons to irradiate the composite structure,
a second detecting plate disposed between the first detecting plate and the composite structure to detect the positron/electron amount produced by the decay of the stopping cosmic-ray muons the composite structure, and
a trigger counter disposed immediately before the composite structure to select the muons,
the positron/electron amount detecting means detects all positron/electron amounts reflection-emitted by the decay of two different muons, positive muons and negative muons, constituting the cosmic-ray muons stopping inside the composite structure, and
the radiography data processing means comprises
a discriminator to sample an input signal from the positron/electron amount detecting means at a predetermined reference clock to remove a noise component from the input signal sampled, and to select only detection signals of the muons,
a field programmable gate array (FPGA), and
an Ethernet connector connecting a ROM circuit to process an output signal from the discriminator and a data processing means.

2. The nondestructive inspection apparatus according to claim 1, wherein the positive muons in the cosmic-ray muons are spin polarized by approximately 30% with respect to the incoming direction.

3. The nondestructive inspection apparatus according to claim 1, wherein the positron/electron amount detecting means detects an intensity of decay electron/positron up to 50 MeV produced by the decay of the cosmic-ray muons.

4. The nondestructive inspection apparatus according to claim 3, wherein
the second detecting plate disposed between the first detecting plate and the composite structure detects the positron/electron amount produced by annihilation of the muons inside the composite structure.

5. The nondestructive inspection apparatus according to claim 4, wherein
the first detecting plate has a position resolution of ±2.50 cm and a sensitive area of 1 m ×1 m, and
the second detecting plate has a position resolution of ±1.25 cm and a sensitive area of 0.5 m×0.5 m.

6. The nondestructive inspection apparatus according to claim 4, wherein the radiography data processing means further comprises
data processing means for processing the output signal from the discriminator to generate radiography information.

7. The nondestructive inspection apparatus according to claim 6, wherein
the composite structure is reinforced concrete,
the first substance is concrete, and
the second substance is a steel rod or a steel frame.

8. The nondestructive inspection apparatus according to claim 7, wherein in the reinforced concrete that is a subject of inspection, the steel rod or the steel frame is in a position having a distance ranging from 10 cm to 20 cm from a surface of the concrete.

9. A nondestructive inspection method for inspecting an inside of a surface layer of a composite structure using cosmic-ray muons traveling substantially in a horizontal direction while being spin polarized by a predetermined amount in a traveling direction, comprising the steps:
(a) sampling with a discriminator, at a predetermined reference clock, a positron/electron amount reflection-emitted having a characteristic time constant in a direction opposite to an irradiation direction of the cosmic-ray muons with annihilation of two different muons, positive muons and negative muons, constituting the cosmic-ray muons stopping inside the composite structure;
(b) removing a noise component from a sampled signal with the discriminator;
(c) screening detection signals of the cosmic-ray muons from the signal with the noise component removed with the discriminator; and
(d) processing the screened detection signals of the positive muons and the negative muons in the cosmic-ray muons with a radiography data processing means to generate radiography information,
wherein an inside of the composite structure is inspected by obtaining the radiography information indicating a state of a second substance, different from a first substance of the surface layer, existing inside the surface layer of the composite structure, and
the nondestructive inspection method is executed by a nondestructive inspection apparatus comprising
positron/electron amount detecting means for detecting the positron/electron amount reflection-emitted having the characteristic time constant in a direction opposite to an incoming direction of the cosmic-ray muons by a decay of the cosmic-ray muons stopping inside the composite structure, and
the radiography data processing means for monitoring the state of the second substance as radiography to output, from the positron/electron amount detected in the positron/electron detecting means,
the positron/electron amount detecting means comprises
a first detecting plate disposed on an incoming side of the cosmic-ray muons to detect a position and a path of the cosmic-ray muons to irradiate the composite structure,
a second detecting plate disposed between the first detecting plate and the composite structure to detect the positron/electron amount produced by the decay of the stopping cosmic-ray muons in the composite structure, and
a trigger counter disposed immediately before the composite structure to select the muons the positron/electron amount detecting means detects all positron/electron amounts reflection-emitted by the decay of two different muons, the positive muons and the negative muons, and the radiography data processing, means comprises the discriminator to sample an input signal from the positron/electron amount detecting predetermined reference clock to remove the noise component from the input signal and to select only the detection signals of the muons, a field programmable gate array (FPGA), and an Ethernet connector connecting a ROM circuit to process an output signal from the discriminator and a data processing means.

10. The nondestructive inspection method according to claim 9, wherein the positive muons in the cosmic-ray muons are spin polarized by approximately 30% with respect to the traveling direction.

11. The nondestructive inspection method according to claim 9, wherein the composite structure is reinforced concrete, the first substance is concrete, and the second substance is a steel rod or a steel frame.

12. The nondestructive inspection method according to claim 11, wherein in the reinforced concrete that is a subject of inspection, the steel rod or the steel frame is in a position having a distance ranging from 10 cm to 20 cm from a surface of the concrete.

13. The nondestructive inspection apparatus according to claim 6, wherein the data processing means is a personal computer.

* * * * *